United States Patent
Shoemaker

(10) Patent No.: US 7,103,921 B1
(45) Date of Patent: Sep. 12, 2006

(54) ADJUSTABLE E-Z HOLD

(76) Inventor: Dorothy M. Shoemaker, 168 Troy Rd., Delaware, OH (US) 43015

( * ) Notice: Subject to any disclaimer, the term of this patent is extended or adjusted under 35 U.S.C. 154(b) by 0 days.

(21) Appl. No.: 11/243,549

(22) Filed: Oct. 5, 2005

(51) Int. Cl.
*A41F 9/00* (2006.01)
(52) U.S. Cl. .......................................... 2/312
(58) Field of Classification Search ............... 2/125, 2/126, 170, 171, 289, 113, 270, 115, 311–312, 2/321, 69, 317, 338, 920, DIG. 11
See application file for complete search history.

(56) References Cited

U.S. PATENT DOCUMENTS

| | | | | |
|---|---|---|---|---|
| 3,086,529 A | * | 4/1963 | Munz et al. ............... | 606/203 |
| 4,393,522 A | * | 7/1983 | Calabrese .................. | 2/336 |
| 4,825,475 A | * | 5/1989 | Smart ........................ | 2/312 |
| 6,339,848 B1 | * | 1/2002 | Mayhood et al. .......... | 2/338 |
| 6,775,846 B1 | * | 8/2004 | LaFauci et al. ............ | 2/125 |

* cited by examiner

*Primary Examiner*—Tejash Patel
(74) *Attorney, Agent, or Firm*—Porter Wright Morris & Arthur, LLP

(57) ABSTRACT

A garter comprising a band comprising an elastic fabric band and a fastener is described. The fabric has a width of from about 0.75 inch to about 1.5 inch. The fastener has a first part coupled to a top surface of a first end the band and a second part coupled to a bottom surface of a second end of the band. The garter may further comprise a sleeve that is slideable along the length of band such that the sleeve covers the portion of the garter where the fastener is coupled when the fastener is fastened.

18 Claims, 4 Drawing Sheets

ADJUSTABLE E-Z HOLD

FIELD OF THE INVENTION

The present invention relates generally to devices for maintaining the position of a compression garment for medical use on a leg or an arm.

BACKGROUND OF THE INVENTION

Elastic compression garments help promote venous and lymphatic return by gently compressing the limb with gradient pressure thereby limiting the amount of swelling and maintaining the reduction in swelling achieved following other treatments.

External compression reduces ultrafiltration from the vasculature, enhances the musculoskeletal pump, increases the re-absorption of fluid into the venous and lymphatic system, reduces the local volume in the veins, and helps maintain the limb shape.

Compression garments may be in the form of a stocking and cover an ankle, the lower leg, a knee, a thigh or an entire leg to the waist. Compression garments are also sleeves and or gloves, used for elbows, hands, the lower arm, an entire arm and the like.

Medical compression garments typically are grouped by compression classes measured in millimeters of mercury (mmHg). These are standardized as:

Class I: 20–30 mmHg
Class II: 3040 mmHg
Class III: 40–50 mmHg
Class IV: 50–60 mmHg In a stocking, these numbers are the compression at the ankle with a gradually decreasing compression gradient to the top of the garment. Many ready-made stockings have a higher stretch fabric over the upper thigh called a mantissa. Garments with the same fabric throughout will give lower compression over a larger diameter body part. Arm sleeves are generally Class I or II, and gloves are typically Class I. Lower extremity garments are generally Class II or III. Additional compression for the leg can be gained by using a higher compression class of garment or by layering a knee-high stocking under or over a longer stocking.

Compression stockings and sleeves are typically made of elastic fabrics. The fibers used are generally latex rubber, synthetic rubbers, nylon, polyester, cotton, or a blend. A stocking or sleeve may be lined with cotton or silk, making the garment more comfortable. Fabrics can be thick or thin, depending on the fibers used and the amount of compression provided. In general, heavier fabrics are used for higher compressions.

There are several styles of garment construction: circular knit, flat knit, and cut and sew. Circular knit fabrics are seamless, but have a tendency to roll down at the top, especially if the area it covers is very fleshy. This creates a tourniquet effect, obstructing flow of fluid from the limb. In a flat knit garment, a flat piece of fabric is knitted to the patient's measurements, and seamed up the back. A cut and sew garment is made of several pieces seamed together. Each of these garments roll less at the top, but rolling is still a problem.

To be effective and comfortable, the garment has to stay in place. A garment that rolls creates a tourniquet-like effect that can cause blood clots. Rolling typically causes pressure that creates an indent in the skin that is painful.

Attempts have been made to create a garment that stays up. Silicone bands or body adhesive used inside the top edge of the garment and are known in the art, but are not adequate. In the case of a stocking, a garter belt, suspenders, or an extension of the garment to the waist are available. Extensions over the shoulder that attach to a bra strap or a diagonal strap across the chest are available for sleeves. Various tapes and even rubber bands have been tried.

None of these devices is acceptable for most patients who are required to wear such garments because they are uncomfortable and ineffective in keeping the top of the garment in place. Adhesives may work initially, but are typically do not last. Tape typically does not adhere to the garment and is difficult to remove from skin, especially skin covered with hair. Existing garters and suspenders may show under clothing, are difficult to put on and are generally uncomfortable. All of these devices may adhere to other clothing.

The condition of the patient's skin is also a consideration. A patient may have wounds or fragile or sensitive skin. The addition of bands or body adhesive is not a universally acceptable means of correcting the problem in that latex and synthetic rubbers may induce an allergic reaction, causing itching, which may result in torn skin from scratching.

A need exists for an independent device for use with an elastic compression garment that is adjustable and can be used with a variety of types of compress bandages and garments, such as all types of stockings and sleeves. A device that is easily adjusted in response to swelling is desired. A need exists for a device that maintains the top of the garment effectively and comfortably without adhering to other clothing.

SUMMARY OF THE INVENTION

The present invention comprises a garter comprising a band comprising a length of elastic fabric and a releasable fastener. The fabric has a width of from about 0.5 inch to about 1.5 inch. The fastener has a first part coupled to a top surface of a first end the band and a second part coupled to a bottom surface of a second end of the band. The garter may further comprise a sleeve that is slideable along the length of band such that the sleeve covers the portion of the garter where the fastener is coupled when the fastener is fastened.

The present invention provides a simple means to keep the upper portion of a compression garment or a bandage from slipping when the garment or bandage is worn by a user. The garment is prevented from slipping toward the end of the extremity without the need for altering the garment, such as requiring a pocket in the garment.

DETAILED DESCRIPTION OF THE INVENTION

Figure 1:
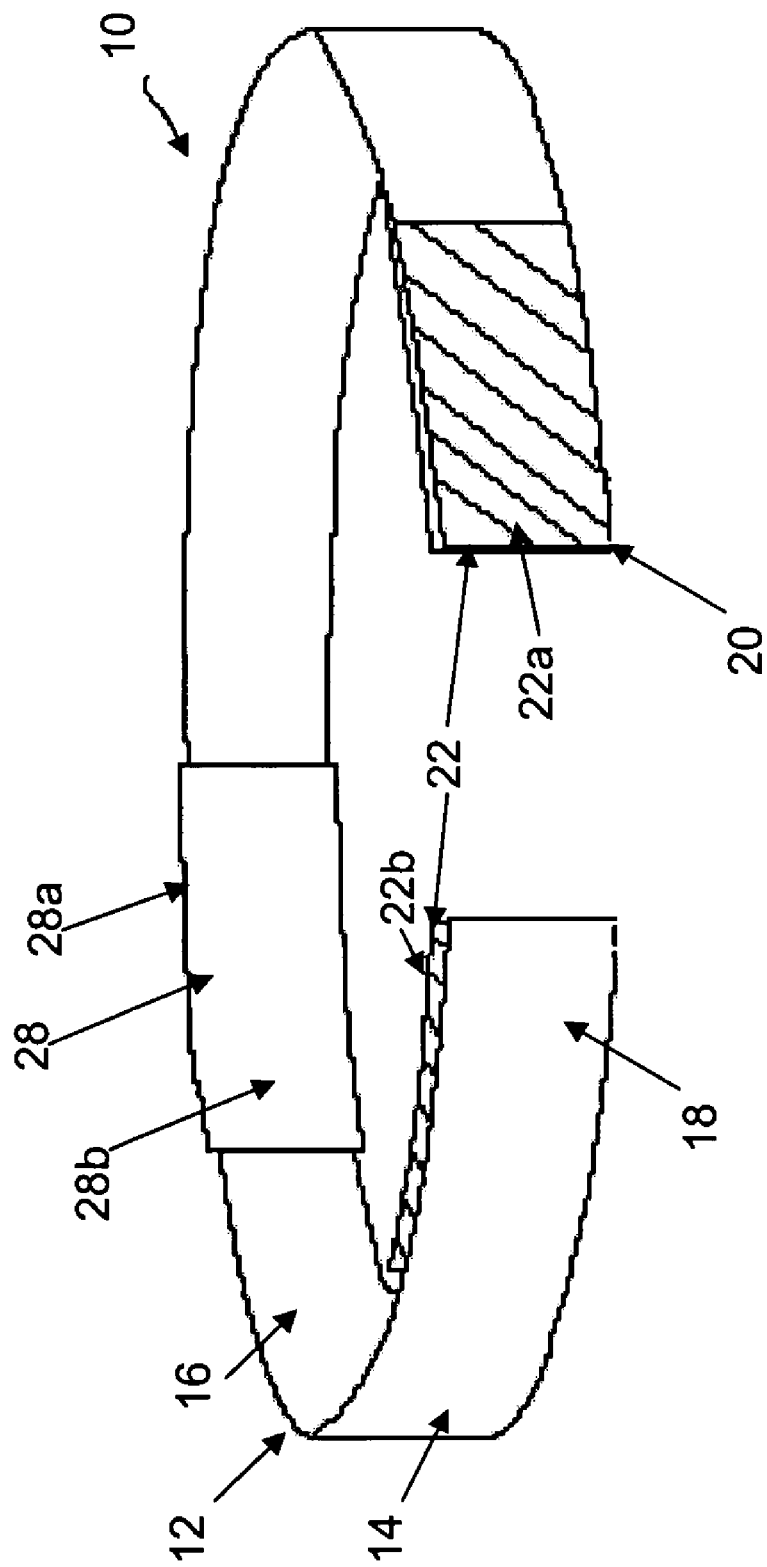
FIG. 1 is a perspective view of the garter of the present invention with a sleeve.

The present invention is directed to a device that securely but removably retains an elastic compression garment. The garter comprises a band and a fastener. Optionally, the garter comprises a sleeve and a tab.

The band is a length of at least one layer of laterally elastic material having a width, a top side and a bottom side and a first end and a second end. Various materials may be used for the band, including most textile materials, polymeric materials, or any other suitable material provided that the material is elastic and washable.

In an embodiment, the band is elastic along its length only. In an embodiment, the width is about 0.5" to about 1.5". In an embodiment, the width of the band is about one inch (1"). The length of the band is variable. In an embodiment, the length of the band varies by the girth of the limb on which it will be used. In an embodiment, the length varies from about 4" in length to a length of over 50". The length of the band may be greater than 50" for use in very large limbs and those suffering from edema. In an embodiment, the length of the band corresponds to a length represented by one of small, medium, large, X-large, XX-large, and XXX-large. In an embodiment, the band is about 17" long. In an embodiment, the length of the band is determined and cut from bulk so that the first end and second ends are generally perpendicular to the sides of the length.

The garter comprises at least one fastener for detachably attaching the ends of the band to itself in a secure and adjustable fashion. The fastener of the present invention is a two part fastener with a first part attached to the top side of the band and a second part attached to the bottom side of the band at each end. The fastener can be any type of fastening structure readily adaptable to the band material, including but not limited to strips of hook and loop fastener fabric, zippers, pins, snaps, hooks, eyes, buckles, ties, buttons, buttonholes, and the like. In an embodiment, the fastener is snag-free Velcro®. In an embodiment, the garter comprises one fastener, however more than one or a combination of different types of fasteners may be employed.

In an embodiment, the fastener is cooperating strips of hook and loop fastener fabric. In an embodiment, the width of the strips of hook and loop fastener fabric is slightly less than the width of the band. In an embodiment, the width of the strips of hook and loop fastener fabric is about ¾" inches wide. In an embodiment, the length of the strips of hook and loop fastener fabric is that sufficient to securely hold the band. In an embodiment, the length of the strips of hook and loop fastener fabric is based on the length of the band. In an embodiment where the band is about 17", the length of the first and second part of the hook and loop fastener fabric is approximately 4" each. Those skilled in the art will appreciate other types of fasteners, quantities, sizes and shapes of means for detachably attaching the garter of the present invention.

The fastener is coupled to the band by any suitable means, such as but not limited to mechanical methods (such as sewing, stapling, buttoning, snapping, and the like); chemical methods (such as gluing or otherwise adhering one material to another); physical methods (such as stamping, heat sealing, and weaving) and the like. In an embodiment where the fastener is a hook and loop fastener, the fastener is coupled to the top and bottom sides of the band by sewing.

Optionally, the garter comprises at least one sleeve. The sleeve is useful for certain types of fasteners to cushion the fastener and or to protect the skin or clothing, such as in the case of some hook and loop fastener fabrics. The sleeve comprises a hollow tube of fabric that fits over the band and is slideable along the length thereof. In an embodiment, the sleeve is made of a smooth fabric such as but not limited to polyester, acrylic, rayon, satin, silk, linen, acetate, cotton and blends thereof. The length of the sleeve is variable. In an embodiment, the sleeve is slightly longer than the length of the fastener. In an embodiment, the sleeve corresponds to the length of hook and loop fastener fabrics exposed after the fastener is fastened.

The present invention provides simple, effective retention of a top edge of an elastic garment. The user applies the garter in a lengthwise fashion to the top of an elastic garment and wraps the garter around the garment just below the top edge of the garment. The user adjusts the tightness of the garter to a tightness preferred by the user and fastens the second end to the first end of the garter thereby encircling the top edge of the garment. In this condition, the garment forms a loop that securely retains the top of the garment. The user may move about without the garment receding down the limb and may tighten or loosen the garter with ease.

In an alternate use, the user has the need to hold a bandage in place prior to slipping a compression garment over an arm or a leg. The user positions the bandage (typically over a wound) then uses the garter to secure the bandage. The user then pulls the compression garment over the garter and the bandage, with the garter holing the bandage in place to prevent slipping. A second garter may be employed on the outside of the garment to hold the top of the garment in place.

Referring now to the drawings, there is shown in FIG. 1 a garter 10. The garter 10 comprises a band 12 of material having a top side 14 and a bottom side 16 and a first end 18 and a second end 20. The band 12 may be made of any elasticized fabric or textile. The band 12 may comprise a single layer of material or more than one layer of material. Suitable materials for the band are numerous, and some desirable properties exist which will help (but which are not functional prerequisites) in the selection of suitable materials. These properties include, but are not limited to, the following: elasticity, durability, structural integrity, stain resistance, and flexibility. The band material preferably should be elastic along its length but not its width. The material preferably should be sufficiently durable so as to be capable of repeated use without ripping, tearing, breaking, or otherwise failing. The band material should be washable. The material for the band 12 is preferably sufficiently soft or smooth so as to minimize irritation or abrasion to the user. The band material preferably is sufficiently resistant to permanent disfigurations after repeated use, such that, upon application of tensile or torsional forces of a magnitude which a human can apply without the use of tools, the material preferably is not be capable of permanent deformations. This is applicable to elasticized materials, where one of the benefits of an elasticized material lies in the ability of the material to return to its original shape. The band material preferably is resistant to stains, soiling, fading, and the like so as to be able to retain its appearance after repeated use. The band material is preferably sufficiently flexible so that the ends 18, 20 of the band 12 can easily be manipulated to allow the first end 18 to be positioned adjacent the second end 20. In an embodiment, suitable materials include substantially any elastic textile material, polymeric materials, or other fabric which would be suitable as an accessory to clothing. In an embodiment, the band 12 is of a single layer of unidirectional elastic fabric.

In an embodiment the size of the garter 10 is determined by the size of the band 12. The band 12 may be of various lengths and widths designed to address placement and size of the user. In an embodiment, a garter 10 is wider and longer for an adult than for a child. In an embodiment, a garter 10 is wider and longer for use with a garment fitted on a leg versus an arm. In the preferred embodiment, the band 12 measures approximately 1 inch wide by approximately 17 inches long.

A fastener 22 comprises a first part 22a and a cooperating second part 22b. The fastener 22 may be of any type commonly known in the art. The fastener 22 first part 22a and second part 22b are disposed generally at the ends 18, 20 of the band 12. The first part 22a of the fastener 22 is coupled to a top side 14 of the band 12 and the second part 22b is coupled to the bottom side 22b of the band 12 at opposite ends 18, 20 of the band 12. This arrangement allows the first part 22a to engage the second part 22b, so that the garter 10 forms a loop when ends 18 and 20 are releasably engaged. The fastener 22 overlays substantially the entire width of the band 12, or only a portion thereof. In an embodiment, the fastener 22 comprises cooperating strips of hook and loop fastener fabric, wherein the first part 22a is a strip of hook fabric, and the second part 22b is a strip of loop fabric. In an embodiment, the width of the first part 22a and of the second part 22b is approximately ¾ inch.

In an embodiment, the first part 22a and the second part 22b are coupled to alternate sides 14, 16 of the band 12 at opposite ends 18, 20 thereof. Alternatively, the first part 22a and the second part 22b may be coupled to the other end 18, 20 and the other side 14, 16 of the band 12.

The circumference of the garter 10 when fastened is adjustable so as to adjust the size of the loop formed by joining first end 18 and second end 20. Adjustability of the garter 10 allows a user to determine tightness while securely retaining the garment. In an embodiment, the length of the fastener 22 provides the adjustability. Generally, the longer the fastener 22, the more adjustable the garter 10.

In an alternate embodiment, the garter 10 may comprise a sleeve 28. The sleeve 28 is a hollow tube that fits over the band 12 such that the sleeve has a front side 28a and a back side 28b. The sleeve 28 front side 28a and back side 28b are slightly wider than the width of the band 12 such that the sleeve 28 freely slides onto and from the band 12 as well as the length of the band 12. The circumference of the hollow tube of the sleeve is sufficient in size to fit over band 12 ends 18, 20 and the fastener 22 when the band 12 is fastened in a loop. The sleeve 28 is made of a material which is not irritative or abrasive to the user. When the garter 10 with a sleeve 28 is used by a user, the sleeve is positioned on the unfastened garter, the user fastens the fastener 22, and slides the sleeve 28 over the fastened fastener and or any exposed surface of the fastener 22.

Figure 2:
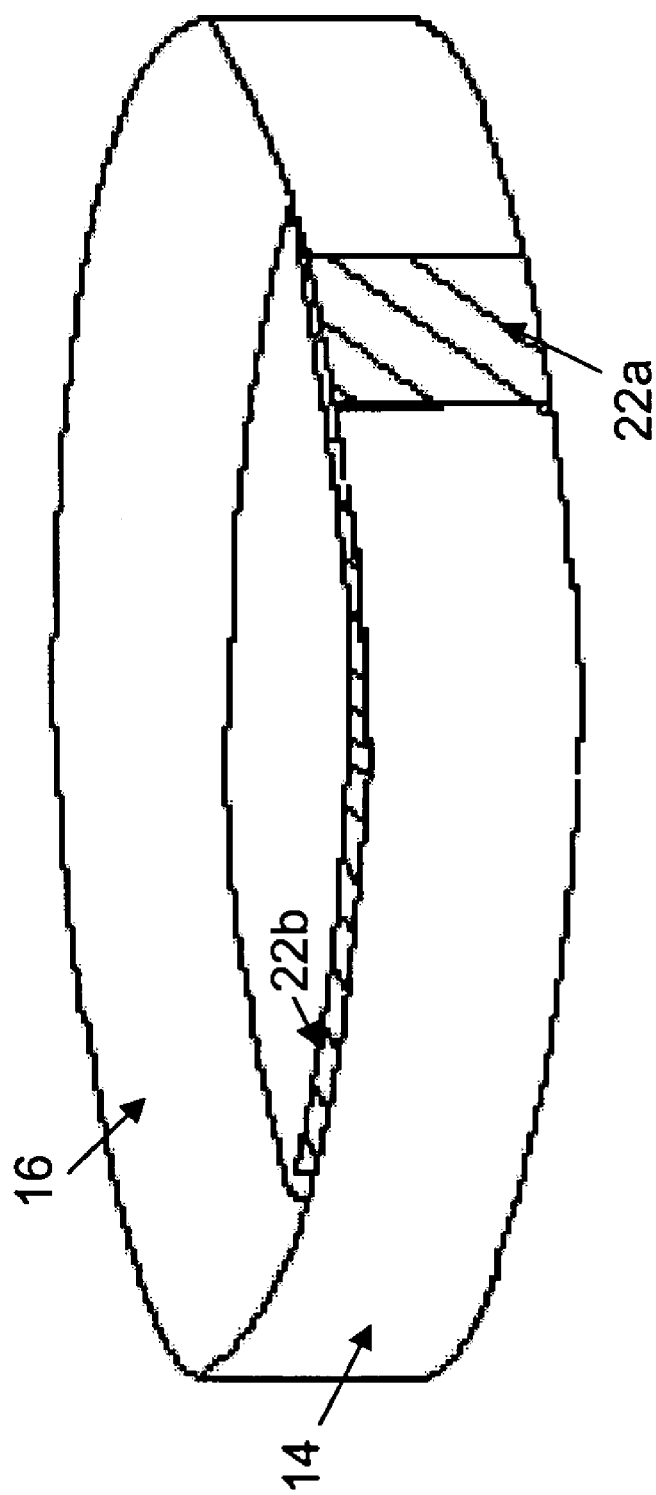
FIG. 2 is perspective view of the garter with the fastener fastened.
Figure 3:
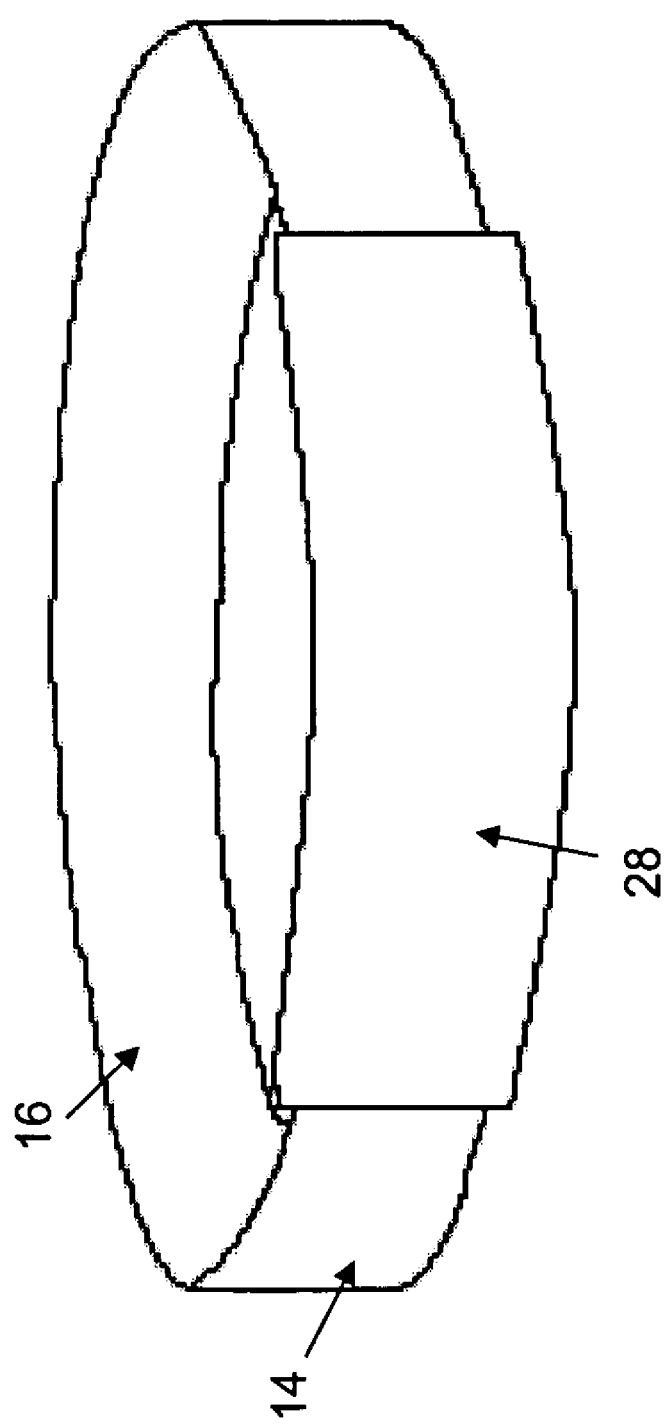
FIG. 3 is perspective view of the garter showing the optional sleeve in place when the fastener is fastened.

FIG. 2 illustrates a garter 10 of the present invention as it appears when the fastener 22 is fastened. FIG. 3 illustrates an embodiment of the present invention showing the garter 10 as it appears when the fastener 22 is fastened and a sleeve 28 is in place over the ends 18, 20 and the fastened fastener 22.

Figure 4:
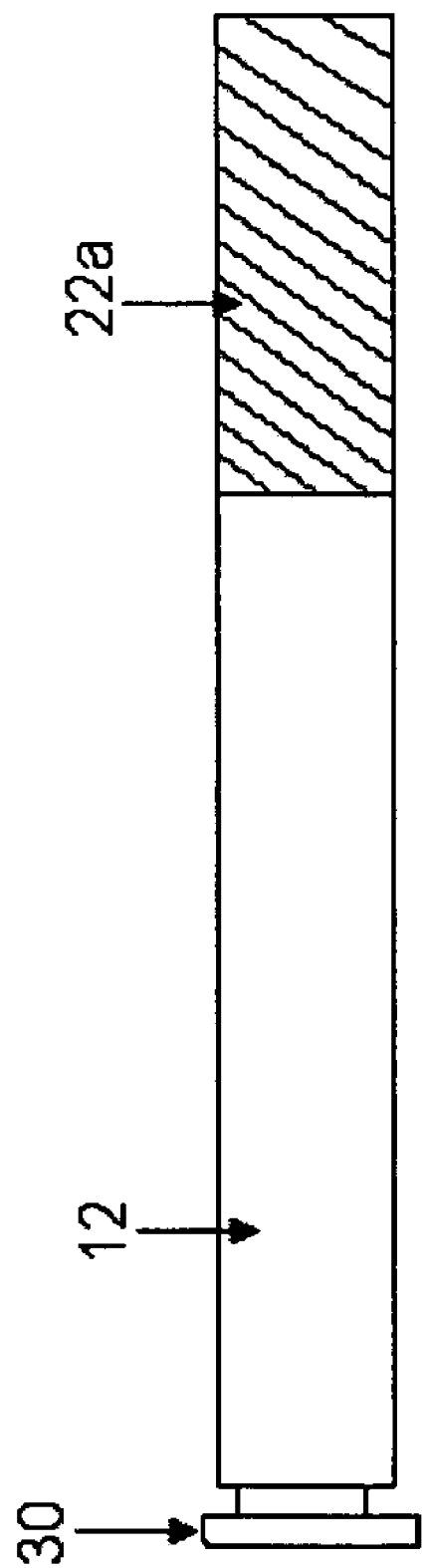
FIG. 4 is a top view of an alternate embodiment of the garter.

In an alternate embodiment depicted in FIG. 4, a fastener 22 is coupled to only one end of the band 12 and the garter 10 comprises a tab 30. The tab is a ring or other similar structure capable of receiving the end of the band with the fastener such that when the fastener 22 is inserted through the tab 30, it can be fastened back upon itself. A sleeve is optionally used. Here, the sleeve is positioned on the unfastened band 12, the band is fastened by looping the free end though the tab 30, and the sleeve is slid into place to cover the tab 30 and or the fastener 22 and or any exposed portion of the fastened fastener 22.

The garter 10 can be easily manufactured in various ways depending on the materials selected for the band 12, the fastener 22, and the optional sleeve 28. Manufacturing the garter 10 comprises, generally, assembling the various component parts. In an embodiment, a length of elastic material is selected and cut from bulk to form the band 12. A length of hook and loop fabric corresponding to the width and length of the band 12 is cut from bulk and separated. A first part 22a of the fastener 22 is coupled to a top side 14 of the band 12 and the second part 22b is coupled to the bottom side 16 of the band 12 at opposite ends 18, 20 of the band 12. In an embodiment, the fastener 22 is sewn to the respective sides and ends.

In an embodiment the sleeve 28 comprises two parts and is sewn together at the edges. In an alternate embodiment, the sleeve is a single piece sewn together along an edge.

In the manufacture of an embodiment comprising a tab 30, the band 12 is cut to the desired length. A first end is inserted through the ring of the tab 30, and secured to itself by means referred to herein. In an embodiment, the securing means is sewing. The fastener 22 is attached to opposite sides 14, 16 of the band 12 at the end opposite the tab 30. The fastener is attached by similar means as those described above. In an embodiment, the securing means is sewing.

The foregoing descriptions of specific embodiments and examples of the present invention have been presented for purposes of illustration and description. They are not intended to be exhaustive or to limit the invention to the precise forms disclosed, and obviously many modifications and variations are possible in light of the above teachings. It will be understood that the invention is intended to cover alternatives, modifications and equivalents. The embodiments were chosen and described in order to best explain the principles of the invention and its practical application, to thereby enable others skilled in the art to best utilize the invention and various embodiments with various modifications as are suited to the particular use contemplated. It is therefore to be understood that within the scope of the appended claims, the invention may be practiced otherwise than as specifically described herein.

I claim:

1. A garter comprising:
   a band comprising a length of elastic fabric, said fabric having a width of from about 0.5 inch to about 1.5 inch;
   a releasable fastener, said fastener having 1) a first part coupled to a top surface of a first end the band and 2) a second part coupled to a bottom surface of a second end of the band; and
   a sleeve, said sleeve slideable along the length of the band such that the sleeve covers the portion of the garter where the fastener is coupled when the fastener is fastened.

2. The garter of claim 1 wherein the garter is used to maintain one of an edge of a compression garment and a bandage.

3. The garter of claim 1 wherein the band is elastic only along the length.

4. The garter of claim 1 wherein the width is about one inch.

5. The garter of claim 1 wherein the length of the band is equal to an average circumference of one of an arm and a leg.

6. The garter of claim 5 wherein the length is about 17 inches.

7. The garter of claim 1 wherein the fastener is a hook and loop fastener.

8. The garter of claim 7 wherein a width of the fastener is slightly less than the width of the band.

9. The garter of claim 8 wherein fastener is about ¾" inches wide.

10. The garter of claim 7 wherein the fastener is a snag-free hook and loop fastener.

11. The garter of claim 9 wherein fastener is approximately 4" in length.

12. The garter of claim 1 wherein the sleeve comprising a hollow fabric tube, said tube having a circumference such that the sleeve fits over the band and is slideable along the length.

13. The garter of claim 11 wherein sleeve is made of a smooth fabric.

14. The garter of claim 13 wherein the sleeve has a length corresponding to the length of a hook and loop fastener exposed after the fastener is fastened.

15. A method of using the garter of claim 1 comprising:
applying the garter in a lengthwise fashion to an item consisting of one of a top of an elastic garment and a bandage;
wrapping the garter around the item such that the fastener is fastenable;
adjusting a circumference of the garter to a tightness preferred by the user;
releasably fastening the second end to the first end.

16. A garter for securing an item consisting of one of a top of an elastic garment and a bandage comprising 1) a band having a width of approximately 1 inch and a length of approximately 17 inches, 2) a hook and loop fastener disposed generally at a top side of a first end of the band and a bottom side of a second end of the band, said fastener having a fastener width of approximately ¾ inches and a fastener length of approximately 4", and 3) a sleeve, said sleeve slideable along the length of the band such that the sleeve covers the portion of the garter where the fastener is coupled when the fastener is fastened, said sleeve comprising a hollow tube, said tube having a circumference sufficient in size to fit over band ends and the fastener when the fastener is fastened.

17. The garter of claim 16 wherein the fastener is coupled the top side and the bottom side of a first end of the band and a tab is coupled to the second end, said tab having an opening, said opening sufficient to receive the band and the fastener coupled to the first end when the first end is inserted though the tab.

18. The garter of claim 17 wherein the sleeve is slid into place to cover one of the tab and an exposed portion of the fastened fastener when the fastener is fastened.

* * * * *